US 6,557,393 B1

(12) United States Patent
Gokhfeld et al.

(10) Patent No.: US 6,557,393 B1
(45) Date of Patent: May 6, 2003

(54) THIN FILM PPB OXYGEN SENSOR

(75) Inventors: Yuzef Gokhfeld, Waltham, MA (US);
Robert H. Hammond, Cambridge, MA (US); Yu Shen, Waltham, MA (US);
Gary Parece, Jamaica Plain, MA (US)

(73) Assignee: Panametrics, Inc., Waltham, MA (US)

( * ) Notice: Subject to any disclaimer, the term of this patent is extended or adjusted under 35 U.S.C. 154(b) by 24 days.

(21) Appl. No.: 09/721,376

(22) Filed: Nov. 22, 2000

(51) Int. Cl.[7] .................. G01N 27/30; G01N 27/406; G01N 27/417
(52) U.S. Cl. .................. 73/23.31; 73/23.2; 73/31.05
(58) Field of Search .................. 73/23.2, 23.31, 73/23.32, 31.01, 31.05

(56) References Cited

U.S. PATENT DOCUMENTS

| 3,941,673 A | * | 3/1976 | Takao et al. ............... 204/427 |
| 4,946,577 A | | 8/1990 | Shibata ....................... 204/427 |
| 4,947,125 A | | 8/1990 | De Pous |
| 5,344,549 A | * | 9/1994 | Dees ........................... 204/425 |
| 6,238,536 B1 | * | 5/2001 | Lundgren et al. .......... 204/426 |

FOREIGN PATENT DOCUMENTS

| EP | 0849591 A1 | | 6/1998 | |
| EP | 0959348 A2 | | 11/1999 | |
| JP | 57-39341 | * | 3/1982 | ............... 73/31.05 |
| JP | 57039341 | | 3/1982 | |
| JP | 57137848 | | 8/1982 | |
| JP | 60-236059 | * | 11/1985 | ............... 73/23.31 |
| JP | 62-198748 | * | 9/1987 | ............... 204/421 |
| JP | 04115153 | | 4/1992 | |
| JP | 5-34308 | * | 2/1993 | ............... 73/23.31 |
| RU | 2022264 C | | 10/1994 | |
| RU | 2053506 C | | 1/1996 | |

* cited by examiner

Primary Examiner—Daniel S. Larkin
(74) Attorney, Agent, or Firm—Iandiorio & Teska (57) ABSTRACT

An oxygen sensor has a sensor body formed of a crystalline material, such as zirconia, with first and second electrodes disposed on a single surface thereof. The electrodes are arranged to induce superionic oxygen transport in the body along current paths extending at a shallow depth in the crystalline material at the electrode surface. The electrodes may be interdigitated or juxtaposed porous electrodes that define an exposed surface pattern of ionic conduction for sensing, and the electrodes are preferably poisoned to inhibit cross sensitivity to reactive components, such as hydrogen, that may be present in the environment. The electrodes may effect electrode-limited superionic conduction in a thin slice of single crystal material, or a polycrystalline yttria-stabilized zirconia film sensing body, and operate at a relatively low temperature in the range of 250–400° C., preferably about 300–350° C., with negligible leakage current or cross sensitivity, allowing reliable measurement of oxygen concentrations in the ppb range. The oxygen sensor may be fabricated together with a heater, such as a resistive heating element, deposited on the back face of the sensor body, or the sensor body may be attached to a heater chip. One such heater chip includes both a heating electrode, and a resistive thermal device that may, for example, provide a feedback or control signal for controlling heater temperature in the desired range. The sensors may be lithographically formed in arrays with suitable lead pads, then scored and separated, and mounted on heater chips, providing a self-contained integrated unit of versatile application.

16 Claims, 6 Drawing Sheets

TFO SENSOR
2 MIL LINE WIDTH
1 MIL SPACE

TFO SENSOR
2 MIL LINE WIDTH
1/2 MIL SPACE

TFO SENSOR
2 MIL LINE WIDTH
1/4 MIL SPACE

TFO SENSOR
2 MIL LINE WIDTH
2 MIL SPACE

TFO SENSOR
2 MIL LINE WIDTH
6 MIL SPACE
ANODE, CATHODE

TFO SENSOR
2 MIL LINE WIDTH
2 MIL SPACE
ANODE, CATHODE, AND
GUARD ELECTRODE

TFO SENSOR
1 MIL LINE WIDTH
1 MIL SPACE

TFO SENSOR
1/2 MIL LINE WIDTH
1/2 MIL SPACE

TFO SENSOR
1/4 MIL LINE WIDTH
1/4 MIL SPACE

TFO SENSOR
1/2 MIL LINE WIDTH
1 1/2 MIL SPACE
ANODE, CATHODE

TFO SENSOR
1/2 MIL LINE WIDTH
1/2 MIL SPACE
ANODE, CATHODE, AND
GUARD ELECTRODE

FIG. 6.

THIN FILM PPB OXYGEN SENSOR

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to oxygen sensors and particularly to oxygen sensors based on superionic conduction between electrodes attached to a solid body formed of an oxide compound, such as yttria stabilized zirconia. Sensors of this general construction may be operated as pumps, to move oxygen through the material which is generally set up as a barrier between a reference environment and an environment to be measured. In this case, the electrodes are energized to induce a current of oxygen ions migrating through the body. They may also be operated as Nernst cells, i.e., batteries in which a potential is induced by the difference in oxygen partial pressures on both sides of the electroded media. In either mode of operation, the electrodes are generally placed across a suitable circuit, and the level of current flow achieved, or the magnitude of the induced potential difference, respectively, provides a measure of oxygen concentration in the surrounding environment. In some practical devices, both forms of operation may be applied: some amount of pumping may be employed to verify, establish, or correct a reference level, followed by reading of a potential difference induced across the wall by the pressure of a sample to be measured. A previously-established formula is then applied to convert the electrical signal to a partial pressure reading.

Typical sensor constructions utilize porous electrodes of platinum or gold. When operated as a pump, oxygen contacting the cathodic surface acquires an electron, initiating ionic migration in the applied electric field gradient to the anode, where it gives up the electron and oxygen is released, passing out through the anode. Ion mobility generally requires that the doped oxide be operated at elevated temperatures, above several hundred degrees Celsius, and up to about 1100 degrees. When operated as a pump, the mechanisms of ion movement in the applied field may be affected by numerous factors, including temperature, thickness, electrode area, and the presence of non-equilibrium conditions within the material from its previous operation, so that the attainment of a repeatable condition may be difficult even when the wall thickness is quite small. These devices usually incorporate a diffusion barrier and pump against a diffusion-limited flow in order to achieve a meaningful measurement. In operation as a Nernst cell, the difference in oxygen pressure results in a higher oxygen/oxide equilibrium point at one surface, and a consequent polarization within the solid material, so a potential appears across the wall. This too depends upon a number of factors, and is affected by the presence on non-equilibrium processes if sufficient settling time is not allowed.

In one form of sensor, a bulk oxide material is shaped into a sensing body with a surface configuration, typically a sheet or tube, that defines a barrier between a reference environment or closed reference cell, and the measurement environment to be tested. Porous platinum electrodes are generally placed on two opposed surfaces the sensor, which operated at a temperature of 500–1200° C. to permit a sufficient level of ionic mobility. After an initial calibration, the Nernst voltage may be read to provide a measure of the oxygen level in the test environment. The reference cell may be periodically replenished by pumping in a reference environment. When operated as a pump, oxygen passing through the porous cathode electrode acquires a charge, and initiates an ionic current flow through the oxide material of the wall toward the anode in the applied gradient. Upon reaching the opposed electrode, ionic oxygen is neutralized and released as gaseous oxygen. These sensors are quite durable; some may be baked out or recalibrated periodically, and may be calibrated in the field by various techniques typically involving the provision of a reference gas on one side of the sensing body. However, the fundamental mechanism of ion flow through a relatively thick body, in dependence upon the oxygen pressure difference existing across that body, results in memory effects and a sensor with relatively slow response and relaxation times.

Another form of a solid superionic oxygen sensor uses doped zirconia or a similar substance in the form of a thin film deposited on a suitable substrate, typically a ceramic, when designed as a pump a diffusion barrier may be incorporated to define the response of the device. These thin film sensors may have shorter ion travel paths, and because of their thin film structure, the electric field gradient between electrodes may be higher and their response and settling times may be shorter. They can also operate at somewhat lower temperatures, e.g., about 350° C., and may be adapted to different operating ranges, but must be somewhat protected form contaminants in the environment, and protected from excessive flow. However, such diffusion barriers may be vulnerable to aging, making sensor parameters and performance unstable over time.

Both kinds of sensors have the drawback that when a background gas such as hydrogen or certain hydrocarbons are present in the mixture being analyzed at low oxygen concentrations, the background gas may result in a faulty reading. This cross-sensitivity problem is particularly severe when the oxygen level is in the ppb range and there is a trace quantity or more of hydrogen. Such conditions may frequently arise in various semiconductor fabrication processes that require monitoring of low oxygen levels. The nature of this interfering effect may possibly involve a hydrogen diffusion current, or may involve electrode-catalyzed burning of the background gas with the oxygen that is present. Whatever its mechanism, the presence of trace hydrogen has been found to defeat or substantially impair the measurement of oxygen concentrations in the low range by these solid oxygen sensors.

Accordingly, it would be desirable to provide an improved oxygen sensor.

It would also be desirable to provide an oxygen sensor having ppb sensitivity.

It would also be desirable to provide an oxygen sensor having ppb sensitivity effective in the presence of hydrogen or background gas.

It would also be desirable to provide an oxygen sensor having reduced cross-sensitivity.

It would also be desirable to provide such a sensor that is fabricated using thin film technology and may be manufactured in quantity and deployed as an electronic chip.

SUMMARY OF THE INVENTION

One or more of these and other desirable features are achieved in accordance with the present invention by an oxygen sensor in which a sensing body formed of a crystalline material, such as zirconia, has electrodes of first and second polarities disposed on a single surface thereof. The electrodes are arranged to induce superionic oxygen transport in the body along current paths extending substantially parallel to the surface at a shallow depth in the crystalline material. The electrodes may be interdigitated or otherwise juxtaposed anodic and cathodic electrodes that define a surface pattern of ion conduction areas for sensing the level of oxygen at the surface. The body of the sensor may be formed as a thin film of polycrystalline material, which is, for example sputtered onto a suitable substrate, but is preferably constructed from a thin slab of single-crystal material. The provision of electrodes on a single side of the device limits the effective ionic conduction to a thin-film region of the electroded surface, and response is governed by electrode area and inter-electrode spacing rather than diffusion properties of a structural wall or a coated barrier. The electrodes are preferably poisoned to inhibit catalytic burning effects. The thin film device so formed operates at a relatively low temperature in the range of 250–400° C., preferably about 300–350° C., with negligible leakage current, and allows measurements of oxygen concentration to be accurately performed in the low ppb range.

The oxygen sensor may be fabricated together with a heater, such as a resistive heating/temperature sensing element deposited on the back face of the crystal, or may be attached to a heater chip to provide a small and integrated unit of versatile construction. The heater chip preferably includes both a heating electrode, and a resistive thermal device that may, for example, provide a feedback or control signal for controlling heater temperature in the desired range. Multiple sensors may be formed lithographically in a large array with suitable lead pads, then scored, separated into single units, and mounted on a heater chip to provide a self-contained integrated unit of versatile application.

BRIEF DESCRIPTION OF THE DRAWINGS

These and other features of the invention will be understood from the description below and accompanying claims, taken together with Figures illustrating illustrative embodiments thereof wherein:

DETAILED DESCRIPTION

Figure 1:
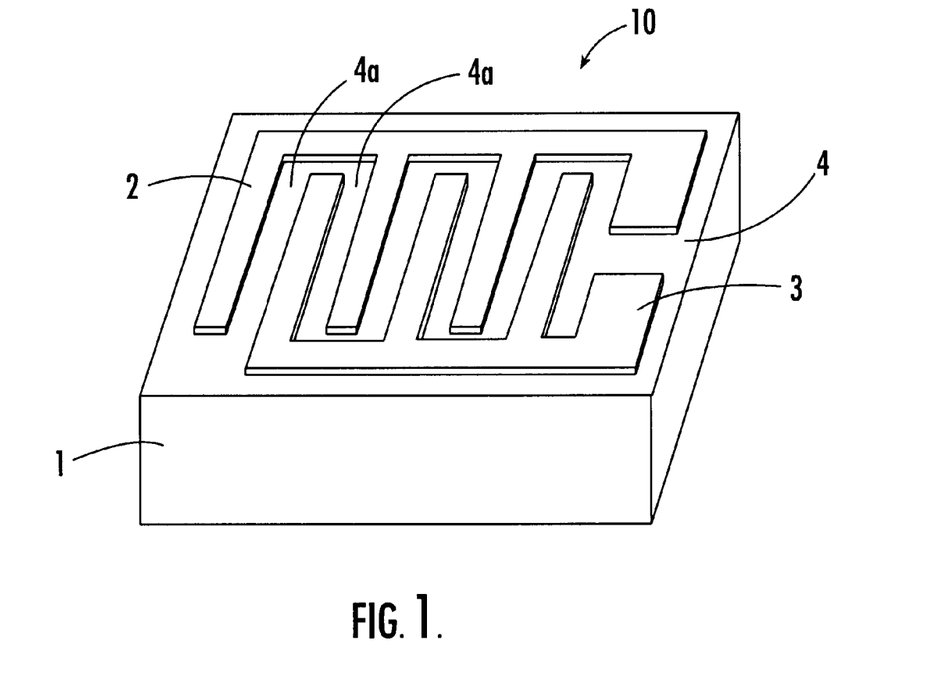
FIG. 1 is a perspective view of an oxygen sensor in accordance with one embodiment of the invention.
Figure 2:
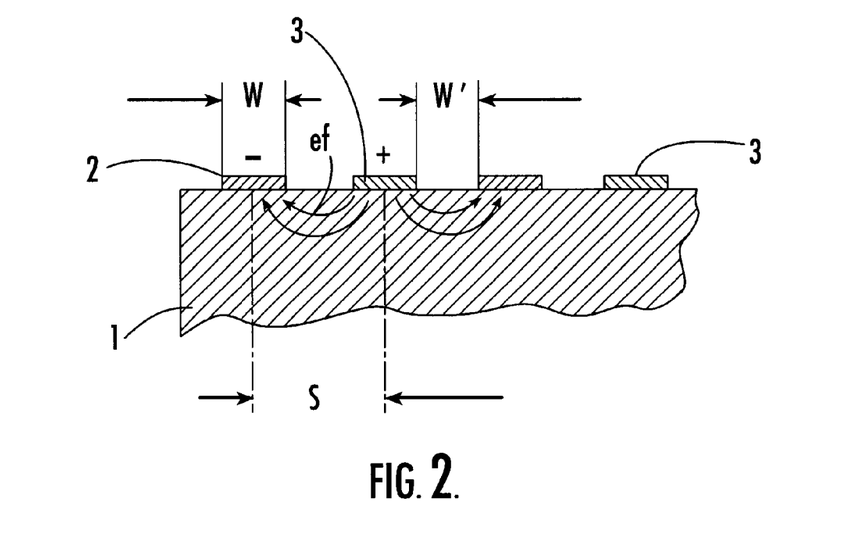
FIG. 2 illustrates a cross-sectional view through the body and electrode structure of the device of FIG. 1.

FIG. 1 illustrates an oxygen sensor 10 in accordance with a basic embodiment of the present invention. The sensor 10 is formed on a substrate body 1 described further below and has a first electrode 2 interposed with a second electrode 3 in a pattern establishing relatively narrow regions 4a therebetween. The electrodes are disposed on a major surface 4 of the body 1, and in the illustrated embodiment comprise two interdigitated combs or sets of fingers. FIG. 2 shows a vertical section through the electrodes 2,3 and the top or near surface portion of the sensing device 10 on which the electrodes lie. As shown, respective fingers of the electrodes 2 and 3 establish electric field or gradient lines ef extending transversely to the fingers and within the body of the sensor 1 at a shallow depth. The field lines run generally between adjacent electrodes. The electrode fingers have a width w,w', respectively, and are spaced at a characteristic spacing s. In the illustrated embodiment, w, and w' are similar, and s is comparable to 2w, so that the width of the gap 4a between electrodes is also w. In many practical embodiments, this gap is between ½w and 2w. Thus, the gap is comparable to the width of the electrodes themselves. In other embodiments, the dimensions need not correspond, even approximately, and the electrode width may be substantially greater than the inter-electrode gap or vice versa. Typically, however, both sets of electrode fingers are preferably of similar width, and provide similar total active areas. As described further below, the electrodes provide a substantial, permeable, region for oxygen to enter and leave the sensor body during operation, and are interposed to provide relatively short ionic current paths therebetween.

The body 1 is preferably made of a yttrium stabilized zirconia, and the electrodes 2, 3 are porous so that oxygen in the surrounding environment passes through one electrode, acquires a charge, and is pumped along the lines ef within the body 1 to the adjacent electrode. Typically, the potential difference between electrodes 2 and 3 is set between about 1.0 and 1.4 volts, sufficiently low that substantially only monovalent ions are created, and the underlying material does not undergo lattice damage or destructive chemical reactions from heating or from higher ionic species. Preferably, the crystalline body 1 is a slab, or slice, or single crystal yttria stabilized zirconia. The level of yttrium may be between approximately five (5) and thirteen (13) percent, most preferably between about eight (8) and ten (10) percent, and the crystal slice may be, for example, approximately twenty mils thick. An oriented slice of <1,0, 0> zirconia such as that commonly available for use as a ceramic substrate for fabrication of various devices may be employed. As shown in this case, the crystalline body extends further below the ion conduction region of paths ef, but the lower, inactive region of the body where the electric field drops off lies outside the ion travel path so that is does not experience transient effects during active operation of the sensor. The back of the sensor thus effectively simply provides additional mechanical or structural strength for the body, and a broad surface through which heat may be coupled from a heater chip. Thus, the overall thickness of the body need not be appreciably greater than the depth of the top surface region of active ionic flow, which varies somewhat with electrode width and spacing, but is roughly only a few mils. The electrodes 2, 3 may have a finger width of approximately (0.2) to about 6.0 mils, and the gaps between electrodes may have a width that is between approximately (0.2) and 6.0 mils. Preferably, for ease of manufacturing, the electrode width is between (0.5) and 2.0 mils. Thus, the chip has an active thickness which is a thin film, and has a comparably short inter-electrode spacing and mean ion path distances.

The electrodes are metallizations, and may generally have a thickness in the range of several hundred to several thousand Angstroms. In one prototype embodiment, the electrodes had a thickness of approximately 500 to 1500 angstroms. By way of overall dimension, suitable prototype embodiments were fabricated on a zirconia body 1 one tenth of an inch square and about twenty mils thick. Different prototypes were fabricated, and electrode widths and electrode gap were each set at a range of size and spacing between electrodes, in various versions of the prototype construction, between one-quarter and two mils. The electrode material was formed of a layer of sputtered platinum followed by a layer of vapor-deposited lead, followed by a further layer of sputtered platinum, the three component sub-layers being of approximately equal thickness, for a total thickness of approximately 500–1500 Angstroms. The amount of lead was selected so that at the intended operating temperature of about 300–350 degrees Celsius, a previously-observed cross-sensitively to trace hydrogen was suppressed. The suppression was believed due to the poisoned electrode being unable to catalyze burning, at the low operating temperature, with the oxygen that was present.

Figure 2A:
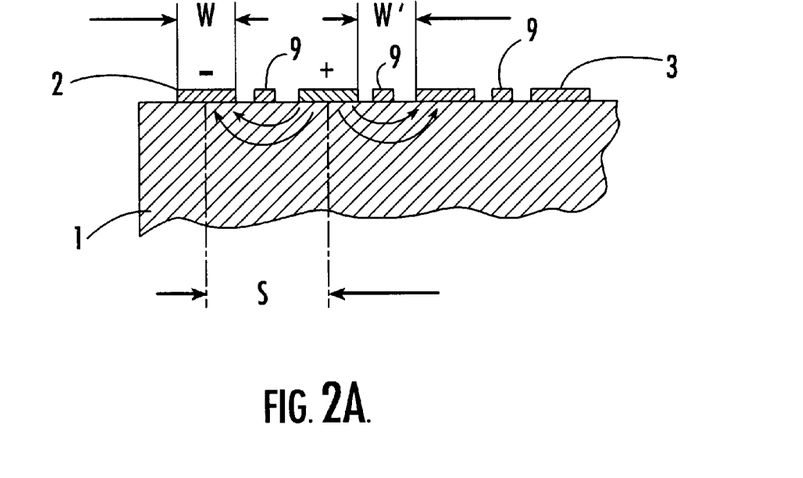
FIG. 2A illustrates a cross-sectional view through the body and electrode structure of another embodiment.

FIG. 2A shows a sectional view similar to that of FIG. 2 of another embodiment, in which guard electrodes g are provided between the anode and cathode. In operation, a different potential or ground may be impressed on the guard electrode to suppress, or to correct, any surface conduction effects that may otherwise occur on the crystal.

Figure 3A:
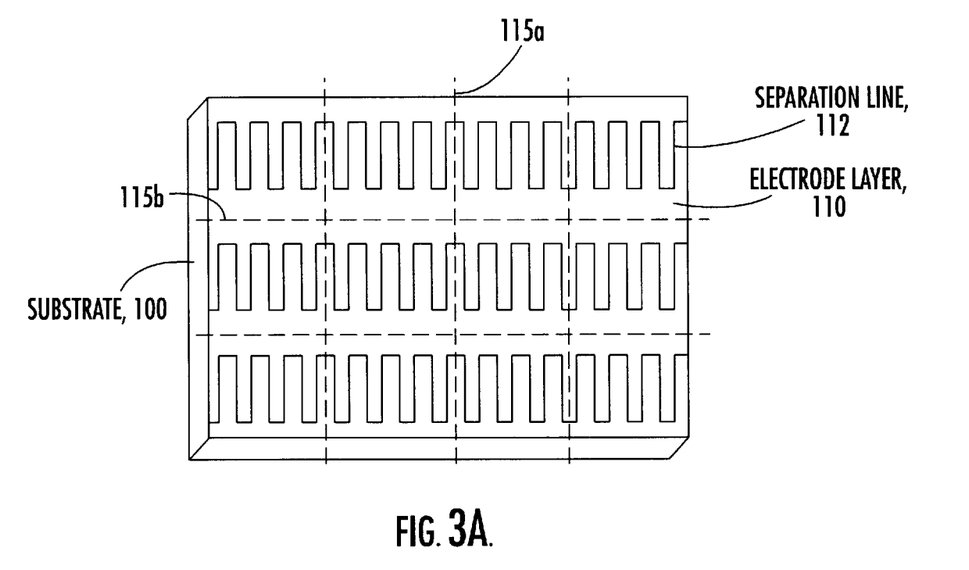
FIGS. 3A–3D illustrate views, in various perspectives, of manufacturing stages or details of the device of FIG. 1.
Figure 3B:
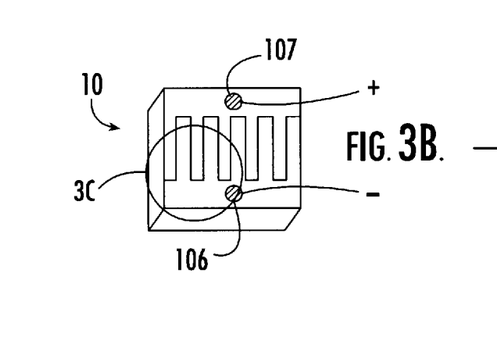
Figure 3C:
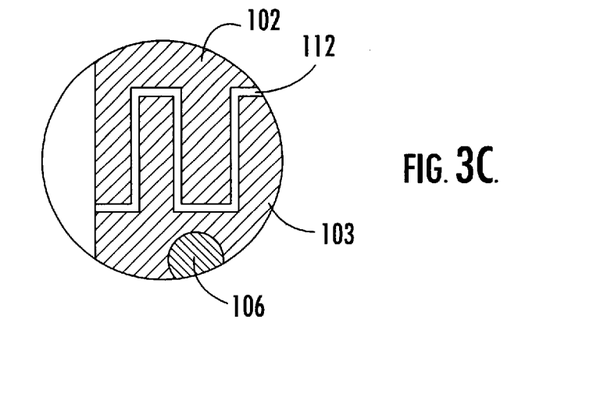
Figure 3D:
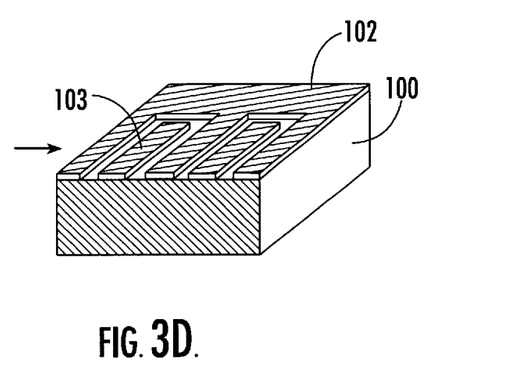

FIGS. 3A through 3D illustrate representative manufacturing steps for forming the oxygen sensor of the present invention in accordance with one method contemplated by applicant. As shown, a bulk substrate substrate 100 is covered with an electrode layer 110 and patterned with a separation line or band 112 to form two separate interdigitated comb patterns extending in one or more ranks along the length of the substrate. The substrate 100 may, for example, comprise a rectangular slab, or a circular section, from a crystalline boule that is intended to form many sensor chips. A sheet cut in the <1,0,0> orientation was used for fabrication and testing of the prototype embodiments, although other crystal orientations as well as sputter-deposited polycrystalline zirconia films are believed to also be useful. As shown in FIG. 3B, individual sensors 10 are formed by scoring and breaking substrate 100 along score lines 115a, 115b such that each sensor includes at least one pair of electrodes that define effective oxygen ionic induction and release areas as described above in connection with FIG. 1.

Leads are connected to respective bond pads 106, 107, which may, for example, be formed by sputtering through a shadow mask. Suitable bond pads may, for example have a layer of about 3000 Angstroms of gold over a chrome or titanium layer several hundred Angstroms thick. As shown in the detailed views of FIG. 3C (in a top plan view) and FIG. 3D (in a section transverse to the major face), the electrode separation band 112 defines the gap between electrodes across which ion migration is to occur in the underlying body of the crystal 100. In one manufacturing process, the surface electrodes are first formed as a single continuous electrode layer, and then the electrode separation band 112 is formed, for example, by laser pattern ablation through a mask, or by etching, or lithographic processes, to separate the continuous single layer into opposed interdigitated cathode and anode electrodes. In the prototype embodiments, rather than starting with a single continuous electrode surface on the major face of the substrate, the electrodes 102, 103 and the separation band 112 were laid down or formed by pattern lithography using a lift-off photolithography process. This was done by first laying down the electrode patterns through a pattern opening etched in a lithography mask in the shape of both desired electrodes, with sputtered platinum to a depth of 200–500 Angstroms. The chip was then removed to a vapor deposition oven for vapor coating of a comparable thickness of lead, after which a comparable thickness of platinum was again sputtered over the two-layer electrode pattern. The lift-off resist was then removed, leaving the desired electrodes. The total electrode thickness was between about 500 and 1500 Angstroms, and constituted a porous surface electrode structure through which environmental oxygen permeates readily. The device so formed was found to operate with accuracy at a relatively low temperature, with test sensors performing well for extended periods at 325° C.

In general, applicant contemplates that the sensor chip 10 will operate at a temperature in the range of 250–500° C., and preferably at a temperature in the range about 300–350°. This temperature is sufficiently low that the described electrode poisoning is effective to inhibit the catalytic burning of background hydrogen which would otherwise occur on the platinum electrode, thus eliminating a major source of cross sensitivity in the sensor readings. Because the chip itself is quite thin, it is not necessary to mount the chip in a large oven. It is preferably mounted on a flat heating device where it essentially resides at or near the surface temperature of the heating device.

Figure 4:
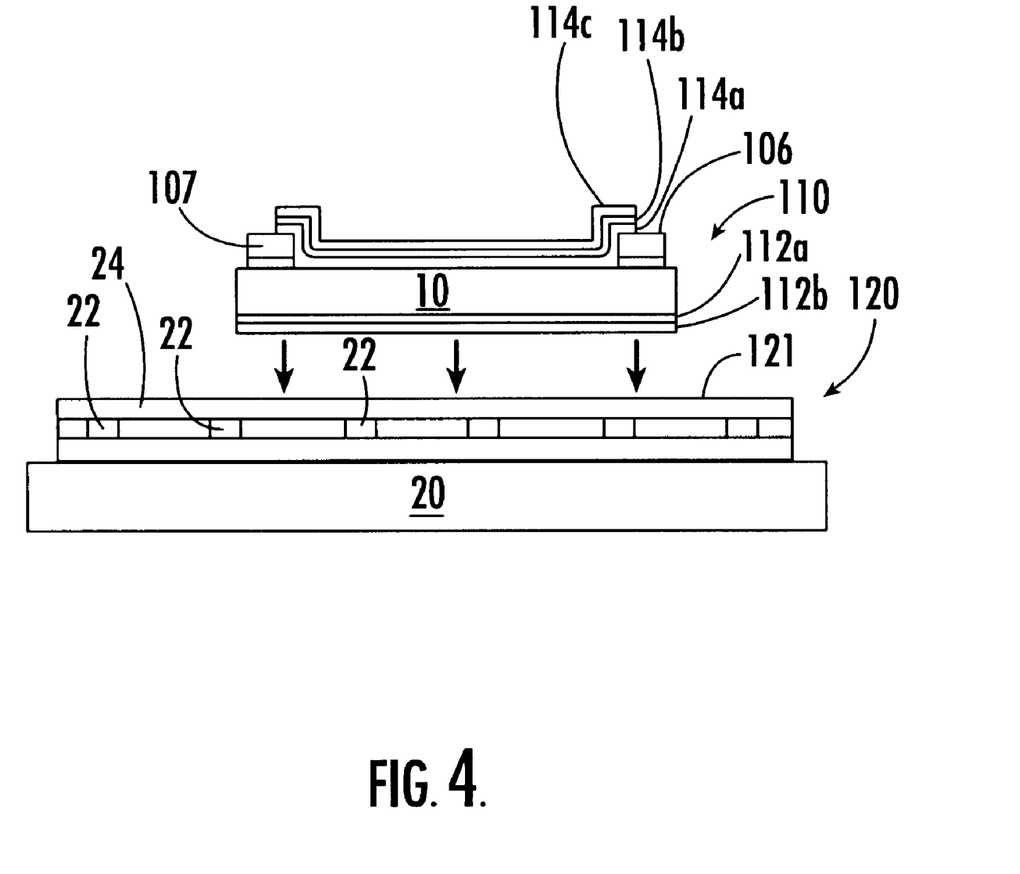
FIG. 4 illustrates a preferred embodiment with a heater.
Figure 5A:
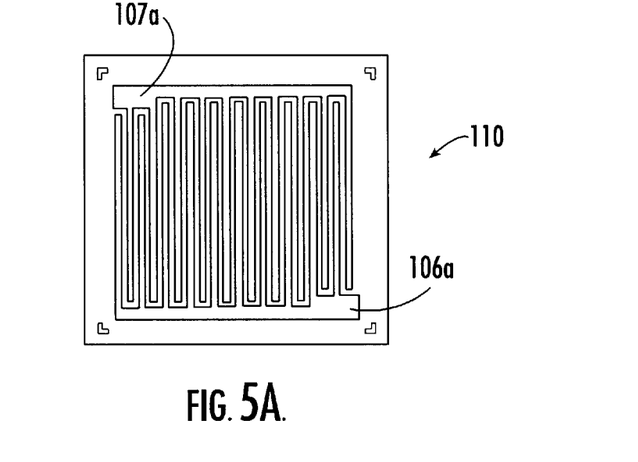
FIGS. 5A and 5B illustrate the sensor portion and the heater portion, respectively, of the embodiment of FIG. 4.

FIG. 4 shows one such embodiment, partially in separated view, of a sensor chip 110 as described above mounted on a heater chip 120. As seen in the vertical section of that view, the chip 110 resides on or is attached to the heating surface 121 of the heating chip 120. For this purpose, on the back or lower surface of the crystal 10, there may be provided a chrome layer 112a covered by a gold layer 112b for die attachment. By way of example, the two-layer die attachment layer may consist of 5000 angstroms of gold deposited over 200 angstroms of chromium or titanium. On the opposite or exposed surface of the sensor body 10, a poisoned porous platinum electrode construction comprising for example platinum, lead, and platinum layers 114a, 114b, and 114c as described above, covers the top surface of the sensor 10, with the pattern electrodes connected to respective bond pads 106, 107 for lead attachment. FIG. 5A illustrates the sensor attached to a heater chip by leads 106a, 107a via these bond pads.

Figure 6:
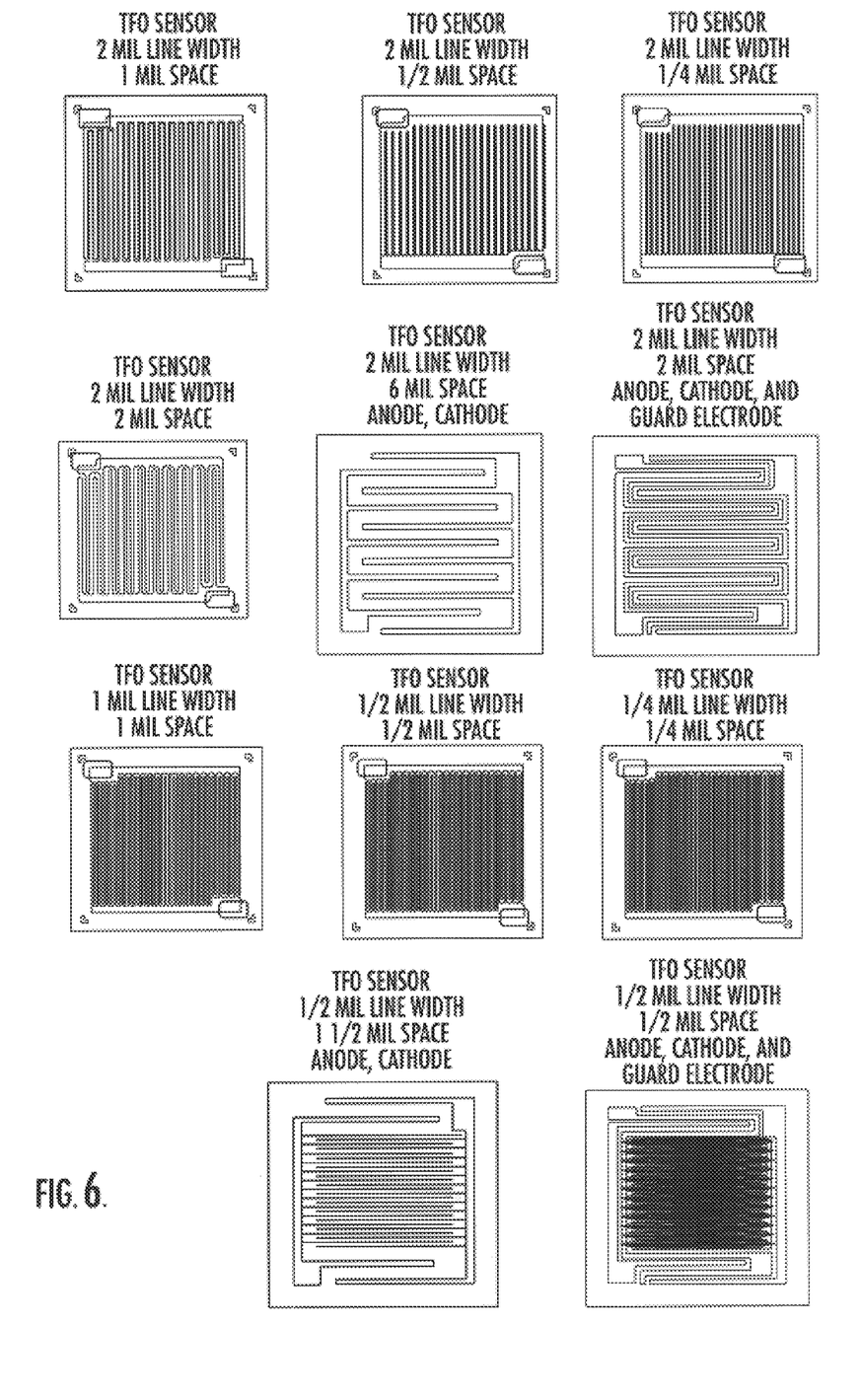
FIG. 6 shows a plurality of electrode dimensional and spacing patterns for the sensors of the invention.

In general, applicant contemplates that the total thickness of the electrode layer may vary from about 500 angstroms to about 5000 angstroms, with the ratio of platinum to lead between 6:1 and 1:2, and the electrodes are either deposited, or are deposited and then treated, so as to achieve porosity that allows permeation of oxygen from the adjacent measuring environment. The bond pads may include a deposit of gold several thousand Angstroms thick over a thinner layer of chromium or titanium, several hundred Angstroms thick. FIG. 6 illustrates a range of suitable electrode widths and spacings for a number of simple interdigitated comb, or comb/guard electrode configurations. Other patterns may be employed.

In the prototype embodiments, all oxygen enters and leaves the sensor from the top, electroded, surface, of which about one-quarter to nine-tenths of the surface area may constitute active electrode area. Furthermore, the ionic current paths corresponding to the field lines ef of FIG. 2, and the mean ion current path length, are all fairly short, extending a length of about one-half to six mils. No diffusion coating is used to limit the rate of oxygen intake or transport. In these circumstances, the ion current is electrode-limited, rather than diffusion-limited, and the electrode configuration achieves stable and repeatable pumping, with the ion current depending directly on the oxygen partial pressure at the surface, operating to produce dependable readings at low temperatures below 350° C. and at low ppb concentrations.

By way of example, the pumping current was found to vary with a power of the partial pressure (approximately the 0.5 power), producing a current that varied between about one nanoAmpere at 1 ppb and about 10–30 nA at 100 ppb oxygen concentration.

By arranging the sensor elements to achieve electrode-limited pumping operation, pump currents may be increased by several orders of magnitude over typical diffusion-limited sensors, and the sensor may reliably detect oxygen partial pressures in the low ppb range. Furthermore, while catalytic burning with, or other cross-sensitivity to, trace gases might normally interfere with measurement accuracy in that low pressure range, applicant has found that the electrodes may be poisoned to effectively address such effects when the operating temperature is maintained sufficiently low.

Figure 5B:
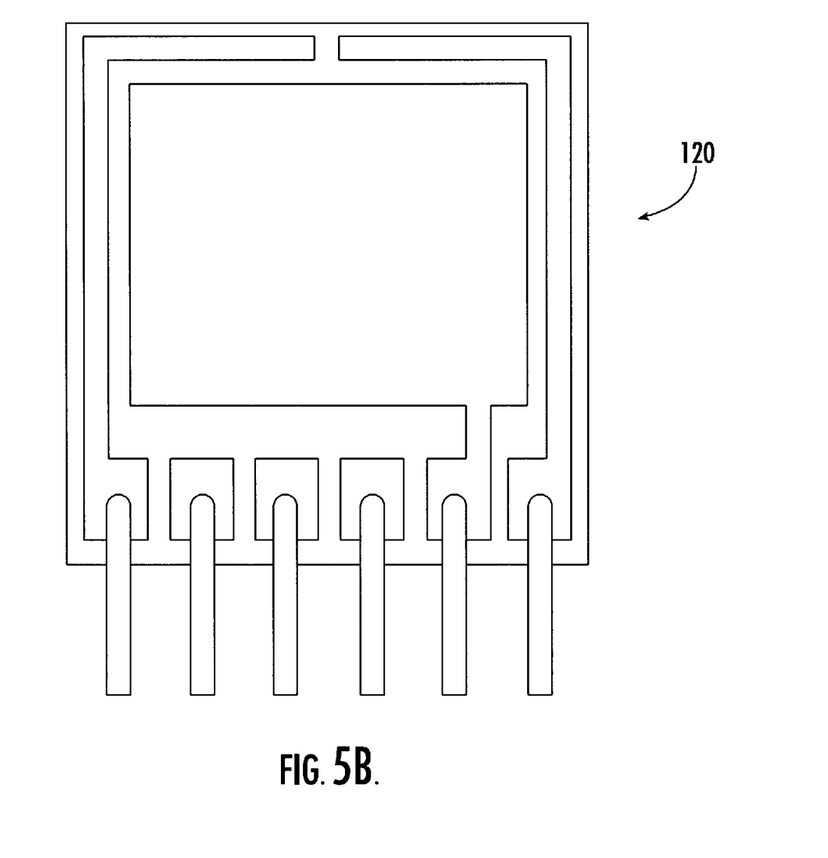
Figure 5C:
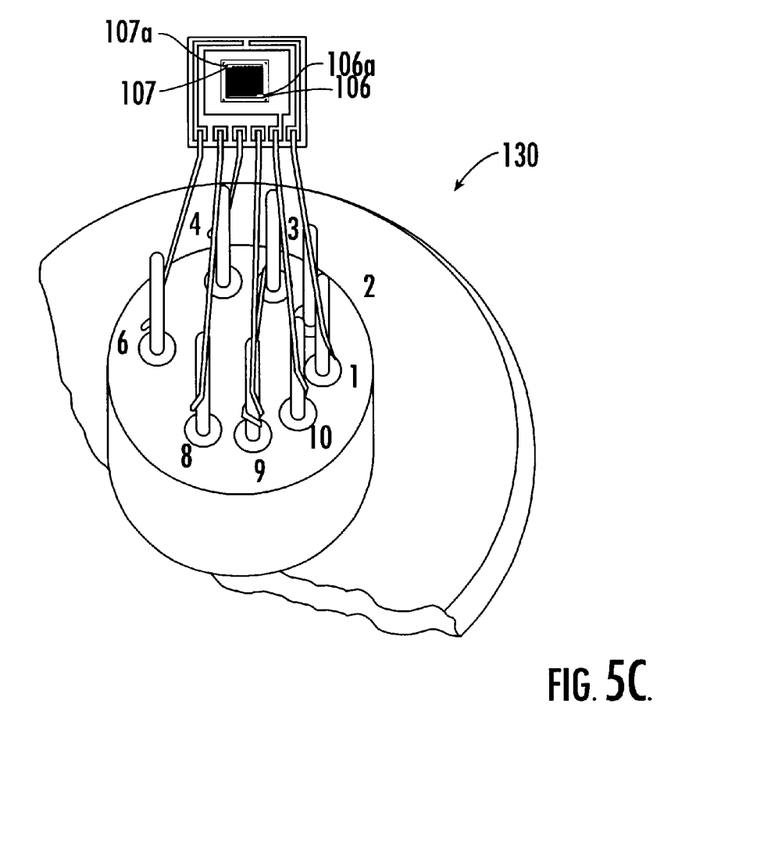
FIG. 5C is a perspective view of the embodiment of FIGS. 4, 5A, and 5B mounted on a standard mounting or base.

As noted above, the sensor chip 10 is preferably contacted to a heater chip 20 to provide an integrated operating sensor unit. Such an integrated unit 130 is shown in FIG. 5C, with a sensor 110 and heater 120 bonded together and mounted on a mounting base.

The heater 120 may be fabricated on a sheet 20 of alumina, for example half a millimeter thick. This may be done by laying down platinum or gold coated nickel leaves 22 in one or more patterns as heaters or resistive sensing electrodes (referred to herein as RTDs or resistive thermal devices) or both, in a multi-layer device, covering the heater/RTD layer with a thick film layer 24 which may, for example, comprise one to three or more glass thick film layers followed by a gold thick film die attachment and bond pad layer (not shown in detail). The latter surface attaches directly to the lower die attachment surface 112b of the sensor 110, and attaches by wire bonds to the bond pads of the sensor electrodes and guard electrodes, if any. By way of example, the heater chip 120 may have approximately twice or more the extent of the sensor chip 110 so that the sensor chip 110 conveniently mounts centrally on the heater chip.

FIGS. 5A and 5B illustrate top plan views of one embodiment of the sensor 110, and the heater 120, respectively. Once attached to each other, the assembly may be mounted in a standard chip case or TF mounting 130, as shown in FIG. 5C.

Applicant contemplates that the sensors of the invention, or the methods of their fabrication may take other forms. By way of example, the electrodes of the sensor unit may have different overall patterns, so long as they provide suitable permeation areas for oxygen ionization and appropriate gaps for fields defining the superionic conduction pathways within the crystalline body. FIG. 6 illustrates a range of dimensions and spacings for several electrode patterns, with and without guard electrodes, which were evaluated in prototyping for the practice of the invention. The maximum and minimum widths or spacings shown therein are not intended to be limiting, but were found to represent a feasible range of constructions that provided effective operating characteristics without requiring excessive attention to manufacturing limitations of the processes employed. Other dimensions of the electrodes, of the sensor chip itself, and related details of the construction may be varied. The electrodes, bond pads, and other conductive structure may be formed by diverse different processes involving suitable masking and photolithography steps, or direct deposit and etching, or ablation steps. Poisoning of electrodes may be accomplished by chemical, physical, or other treatments rather than by direct vapor metallization. Similarly, porosity of the sensor electrode structures, as well as the electrode surface adhesion may be controlled or enhanced by processes known in the chip fabrication or sputtering arts, and other details of construction may be suitably varied.

Applicant also contemplates embodiments wherein chips having two or more regions with different electrode structures or surface characteristics are fabricated together on the same substrate, to be scored and mounted as a single chip having dual- or multi-range capabilities, or wherein chips having two or more regions are mounted on a dual or multi-region heater to provide a unit with the ability to have different measurement ranges, or to have one portion operate while another portion bakes out or is regenerated or purged, or remains dormant until needed, thus providing more extended or continuous operation.

The invention being thus disclosed and illustrative embodiments depicted herein, further variations and modifications of the invention will occur to those skilled in the art, and all such variations and modifications are considered to be within the scope of the invention, as defined by the claims appended hereto and equivalents thereof.

What is claimed is:

1. An oxygen sensor comprising:
   a crystalline body having a major surface;
   a first electrode extending over said major surface; and
   a second electrode extending over said major surface, said first and second electrodes being interposed to define regions of oxygen ion conduction therebetween through said crystalline body substantially at said major surface, wherein at least one of said first electrode and said second electrode is poisoned above but not at an interface between the at least one electrode and the crystalline body.

2. The oxygen sensor of claim 1, wherein said first electrode and said second electrode are porous.

3. The oxygen sensor of claim 1, wherein the poisoned electrode is a platinum electrode poisoned by lead.

4. The oxygen sensor of claim 1, wherein the first and second electrodes include an amount of platinum effective to permit ionization of oxygen entering said crystalline body and are poisoned to a level effective to inhibit cross sensitivity to trace gases other than oxygen whereby ionic current between said electrodes effectively indicates oxygen concentration at said major surface.

5. The oxygen sensor of claim 1, further comprising a heater in thermal contact therewith.

6. The oxygen sensor of claim 5, wherein said heater includes a chip having a heating element for heating the chip and a resistive thermal element for providing a feedback signal to control chip temperature.

7. The oxygen sensor of claim 5, wherein said sensor is affixed to the heater and is operable to maintain a fixed temperature between 250 and 400 degrees Celsius.

8. The oxygen sensor of claim 7, operable to maintain a fixed temperature of about 300–350 degrees Celsius.

9. The oxygen sensor of claim 1, wherein said body includes a sheet of single crystal zirconia.

10. The oxygen sensor of claim 9, wherein said single crystal zirconia is yttrium-stabilized zirconia.

11. The oxygen sensor of claim 1 wherein at least one of the first and the second electrodes includes a platinum layer disposed on the major surface of the crystalline body and a lead layer disposed on the platinum layer so that the lead poisoning does not reach the interface between the at least one of the first and the second electrodes and the crystalline body.

12. The oxygen sensor of claim 11 wherein at least one of the first and the second electrodes includes a second platinum layer disposed on the lead layer.

13. A method of measuring oxygen concentration, such method comprising the steps of:
- providing a crystalline body having a major surface;
- providing a first electrode extending over said major surface;
- providing a second electrode interposed with said first electrode to define a region of oxygen ion conduction between the first and the second electrode along current paths extending through said crystalline body and substantially parallel to said major surface; and
- poisoning at least one of said electrodes above but not at an interface between the at least one electrode and the crystalline body.

14. An oxygen sensor comprising:
- a thin film of crystalline oxide; and
- first and second porous poisoned electrodes disposed on one surface of said thin film for defining an electrode-limited ionic current in said film at said surface, such that application of a potential to said electrodes produces an ionic current representing oxygen partial pressure at said surface, wherein said porous poisoned electrodes are poisoned above but not at said surface.

15. An oxygen sensor comprising:
- a crystalline body having a major surface;
- a first electrode extending over said major surface; and
- a second electrode extending over said major surface, said first and second electrodes being interposed to define regions of oxygen ion conduction therebetween through said crystalline body substantially at said major surface, wherein at least one of the first and the second electrodes includes a platinum layer disposed on the major surface of the crystalline body and a poisoning lead layer disposed on the platinum layer so that the lead poisoning does not reach the interface between the at least one of the first and second electrodes and the crystalline body.

16. The oxygen sensor of claim 15 wherein at least one of the first and the second electrodes includes a second platinum layer disposed on the lead layer.

* * * * *